(12) United States Patent
Xiao et al.

(10) Patent No.: US 11,954,852 B2
(45) Date of Patent: Apr. 9, 2024

(54) MEDICAL IMAGE CLASSIFICATION METHOD, MODEL TRAINING METHOD, COMPUTING DEVICE, AND STORAGE MEDIUM

(71) Applicant: TENCENT TECHNOLOGY (SHENZHEN) COMPANY LIMITED, Shenzhen (CN)

(72) Inventors: Kaiwen Xiao, Shenzhen (CN); Xiao Han, Shenzhen (CN); Hu Ye, Shenzhen (CN); Niyun Zhou, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 426 days.

(21) Appl. No.: 17/375,177

(22) Filed: Jul. 14, 2021

(65) Prior Publication Data
US 2021/0343012 A1 Nov. 4, 2021

Related U.S. Application Data

(63) Continuation of application No. PCT/CN2020/096797, filed on Jun. 18, 2020.

(30) Foreign Application Priority Data

Jun. 21, 2019 (CN) .......................... 201910543018.9

(51) Int. Cl.
*G06T 7/00* (2017.01)
*G06T 3/4007* (2024.01)
(Continued)

(52) U.S. Cl.
CPC .......... *G06T 7/0012* (2013.01); *G06T 3/4007* (2013.01); *G06T 7/90* (2017.01);
(Continued)

(58) Field of Classification Search
CPC ....... G06T 7/0012; G06T 3/4007; G06T 7/90; G06T 2207/10056; G06T 2207/20076;
(Continued)

(56) References Cited

U.S. PATENT DOCUMENTS

2018/0253624 A1    9/2018  Schafer et al.
2019/0019282 A1*   1/2019  Atzmon ................ G06T 1/0028
(Continued)

FOREIGN PATENT DOCUMENTS

CN        103581672 A      2/2014
CN        105100789 A     11/2015
(Continued)

OTHER PUBLICATIONS

"Super-resolution image restoration based on maximum-likelihood estimation," Chinese Journal of Scientific Instrument, vol. 29, No. 5, May 2008, 6 pages.
(Continued)

*Primary Examiner* — Qian Yang
(74) *Attorney, Agent, or Firm* — Crowell & Moring LLP

(57) ABSTRACT

This application describes a medical image classification method, a model training method, and a server. The medical image classification method includes: obtaining, by a device, a medical image data set. The device includes a memory storing instructions and a processor in communication with the memory. The method includes performing, by the device, quality analysis on the medical image data set, to extract feature information of a medical image in the medical image data set; and classifying, by the device, the medical image data set based on the feature information and by using a pre-trained deep learning network for performing anomaly detection and classification, to obtain a classification result.

14 Claims, 10 Drawing Sheets

(51) Int. Cl.
  *G06T 7/90* (2017.01)
  *G16H 30/20* (2018.01)
  *G16H 30/40* (2018.01)
(52) U.S. Cl.
  CPC .............. *G16H 30/20* (2018.01); *G16H 30/40* (2018.01); *G06T 2207/10056* (2013.01); *G06T 2207/20076* (2013.01); *G06T 2207/20081* (2013.01); *G06T 2207/20084* (2013.01); *G06T 2207/30004* (2013.01); *G06T 2207/30168* (2013.01)
(58) Field of Classification Search
  CPC . G06T 2207/20081; G06T 2207/20084; G06T 2207/30004; G06T 2207/30168; G06T 2207/30024; G06T 2207/30096; G06T 1/20; G06T 5/002; G06T 7/13; G06T 7/155; G16H 30/20; G16H 30/40; G16H 50/20; G16H 50/70; G06N 3/045; G06N 3/08
  See application file for complete search history.

(56) References Cited

U.S. PATENT DOCUMENTS

| | | | |
|---|---|---|---|
| 2020/0005931 A1* | 1/2020 | Madabhushi | A61B 5/4381 |
| 2020/0129114 A1* | 4/2020 | Griffith | A61B 5/459 |

FOREIGN PATENT DOCUMENTS

| | | |
|---|---|---|
| CN | 106651834 A | 5/2017 |
| CN | 106991439 A | 7/2017 |
| CN | 107066934 A | 8/2017 |
| CN | 107729948 A | 2/2018 |
| CN | 107862249 A | 3/2018 |
| CN | 108364017 A | 8/2018 |
| CN | 109118442 A | 1/2019 |
| CN | 109522960 A | 3/2019 |
| CN | 109544503 A | 3/2019 |
| CN | 109815965 A | 5/2019 |
| CN | 110232719 A | 9/2019 |
| CN | 110428475 A | 11/2019 |

OTHER PUBLICATIONS

International Search Report with concise English translation and Written Opinion regarding PCT/CN2020/096797 dated Sep. 23, 2020.
First Chinese Office Action with concise English translation regarding CN201910543018.9 dated Sep. 15, 2020.
Second Chinese Office Action with concise English translation regarding CN201910543018.9 dated May 7, 2021.
Chenxp2311, Caffe: MNIST database format conversion, read and write LMDB database with python with Abstract, CSDN, dated Jul. 15, 2016.
Xuehaiwuya GL, Caffe: MNIST database format conversion, read and write LMDB database with python with Abstract, 360doc.com, dated Feb. 22, 2017.
Park S.C. et al., Super-resolution image reconstruction: A technical overview, IEEE Signal Processing Magazine, vol. 20, Issue 2, dated Dec. 31, 2003.

* cited by examiner

MEDICAL IMAGE CLASSIFICATION METHOD, MODEL TRAINING METHOD, COMPUTING DEVICE, AND STORAGE MEDIUM

RELATED APPLICATION

This application is a continuation application of PCT Patent Application No. PCT/CN2020/096797, filed on Jun. 18, 2020, which claims priority to Chinese Patent Application No. 201910543018.9, filed with the National Intellectual Property Administration, PRC on Jun. 21, 2019, both of which are incorporated herein by reference in their entireties.

FIELD OF THE TECHNOLOGY

This application relates to a medical image classification method, a model training method, and a server, and specifically, to a microscopic image classification method, a model training method, a computing device, and a storage medium.

BACKGROUND OF THE DISCLOSURE

Pathological verification analysis is an important reference of a final determination standard in clinical medicine, and a main process thereof is to obtain corresponding tissue cells from tissue of a sick body, and confirm an illness state by observing and analyzing a manufactured pathological tissue section under a microscope. As the medical level is continuously improved, microscopic pathological image data breaks out in a blowout manner, and the quantity of digital microscopic pathological images increases geometrically.

SUMMARY

In view of this, this application provides various embodiments for a medical image classification method, a model training method, a computing device, and a storage medium.

The present disclosure describes a method for classifying a medical image. The method includes obtaining, by a device, a medical image data set. The device includes a memory storing instructions and a processor in communication with the memory. The method includes performing, by the device, quality analysis on the medical image data set, to extract feature information of a medical image in the medical image data set; and classifying, by the device, the medical image data set based on the feature information and by using a pre-trained deep learning network for performing anomaly detection and classification, to obtain a classification result.

The present disclosure describes an apparatus for classifying a medical image, the apparatus includes a memory storing instructions; and a processor in communication with the memory. When the processor executes the instructions, the processor is configured to cause the apparatus to: obtain a medical image data set, perform quality analysis on the medical image data set, to extract feature information of a medical image in the medical image data set, and classify the medical image data set based on the feature information and by using a pre-trained deep learning network for performing anomaly detection and classification, to obtain a classification result.

The present disclosure describes a non-transitory computer-readable storage medium, storing computer-readable instructions. The computer-readable instructions, when executed by a processor, are configured to cause the processor to perform: obtaining a medical image data set; performing quality analysis on the medical image data set, to extract feature information of a medical image in the medical image data set; and classifying the medical image data set based on the feature information and by using a pre-trained deep learning network for performing anomaly detection and classification, to obtain a classification result.

An embodiment of this application provides a medical image classification method, performed by a computing device. The method includes: obtaining a medical image data set; performing quality analysis on the medical image data set, to extract feature information of a medical image; and classifying the medical image based on the extracted feature information and by using a pre-trained deep learning network for performing anomaly detection and classification on the medical image, to obtain a classification result.

An embodiment of this application further provides a training method for a model for performing anomaly detection and classification on a medical image, performed by a computing device, the method including: obtaining an original medical image data set and a corresponding original image annotation information set; performing quality analysis on the original medical image data set, to extract feature information of an original medical image; and training, based on the extracted feature information in the original medical image data set and the original image annotation information set, a deep learning network for performing anomaly detection and classification on the medical image, to obtain a trained deep learning network model for performing anomaly detection and classification on the medical image.

An embodiment of this application further provides a medical image classification apparatus. The apparatus includes an obtaining module, a quality analysis module, and a classification module. The obtaining module is configured to obtain a medical image data set. The quality analysis module is configured to perform quality analysis on the medical image data set, to extract feature information of the medical image. The classification module is configured to classify the medical image based on the extracted feature information and by using a pre-trained deep learning network for performing anomaly detection and classification on the medical image, to obtain a classification result.

An embodiment of this application further provides a training apparatus for a model for performing anomaly detection and classification on a medical image. The training apparatus includes an obtaining module, a quality analysis module, and a training module. The obtaining module is configured to obtain an original medical image data set and a corresponding original image annotation information set. The quality analysis module is configured to perform quality analysis on the original medical image data set, to extract feature information of an original medical image. The training module is configured to train, based on the extracted feature information in the original medical image data set and the original image annotation information set, a deep learning network for performing anomaly detection and classification on the medical image, to obtain a trained deep learning network model for performing anomaly detection and classification on the medical image.

An embodiment of this application further provides a computing device, including: a memory, a processor, and a computer program stored on the memory and executable on the processor, the processor, when executing the program, implementing the method according to the embodiments of this application. An embodiment of this application further provides a medical image classification system, including a medical image obtaining device and a medical image processing device; the medical image obtaining device being configured to scan a medical image and transmitting the medical image to the medical image processing device; and the medical image processing device being configured to perform any method according to the embodiments of this application.

An embodiment of this application further provides a non-volatile computer-readable storage medium, storing a computer program executable by a computer device, the program, when run on the computer device, causing the computer device to perform the method according to the embodiments of this application.

BRIEF DESCRIPTION OF THE DRAWINGS

The embodiments of this application are described in more detail and with reference to accompanying drawings.

DESCRIPTION OF EMBODIMENTS

Figure 1:
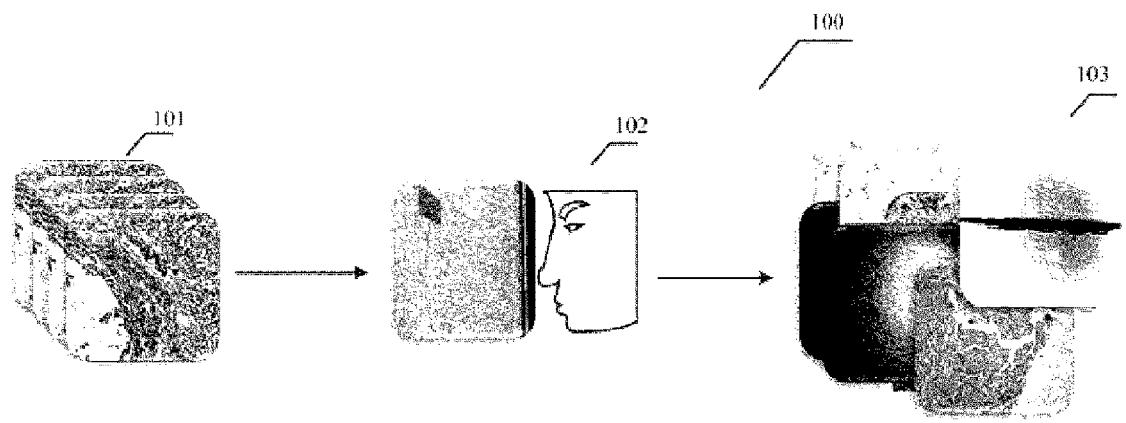
FIG. 1 shows a method for screening microscopic images according to the related art.

The following descriptions provide particular details for fully understanding and implementing various embodiments of this application. A person skilled in the art is to understand that, technical solutions of this application may be implemented in some cases that the details do not exist. In some cases, some well-known structures and functions are not shown or described in detail, to avoid unnecessarily blurring the descriptions of the embodiments of this application. Terms used in this application are understood in a most widely proper manner, even if the terms are used with reference to particular embodiments of this application.

The AI technology is a comprehensive discipline, and relates to a wide range of fields including both hardware-level technologies and software-level technologies. The basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning/deep learning.

Currently, deep learning is a technology of machine learning and one of research fields. Artificial intelligence (AI) is implemented in a computer system by building an artificial neural network with a hierarchical structure.

Due to successful application of deep learning (DL) in the field of vision, researchers also introduce the DL to the field of image processing such as the field of medical image processing, and a deep learning neural network model is trained by using a large quantity of training images to enable the model to perform image processing, for example, perform quality analysis on a medical image to classify the medical image such as filter out an invalid or unqualified pathological image.

Currently, analysis for a microscopic pathological image mainly depends on manual review. During manual review by a human being, a medical image is annotated mainly by a medical worker to obtain an abnormal condition, and then the abnormal condition is fed back to a medical institution or medical expert for confirmation.

Moreover, quality analysis of a microscopic image is mainly that a pathological doctor or another medical expert repeats precise annotation to raise anomaly, perform quality evaluation, and eliminate noise information. In some cases, a trained technician obtains anomaly result representation, and feeds back the noise data to a medical institution or medical expert for confirmation. In this way, not only the efficiency is low, but also it is extremely easy to introduce low-quality data or invalid data. The existing microscopic image annotation technology has low annotation reliability, high costs, and a long period of obtaining valid data.

Therefore, an embodiment of this application provides a medical image classification method, where among a huge quantity of pathological images into which a large quantity of invalid and unqualified microscopic pathological images are mixed, pathological images may be described through digital image morphology descriptions (including, for example, hue, saturation, lightness, definition, texture, and an entropy value), thereby filtering out unqualified microscopic pathological images, and reducing noise confusion caused by microscopic pathological images to disease diagnosis.

Before the medical image classification method provided in the embodiments of this application is described, first, some terms in the embodiments of this application are described, to facilitate understanding by a person skilled in the art.

Defocus: When an objective lens of a microscope is focused on a pathological section, or a camera cannot reach or exceed a proper object distance, a blurred microscopic image is formed.

Hole, overlapping, and folding of section cells: During section manufacturing, because section operators are different, hole, overlapping, and folding occur during manufacturing of section cells; and the cells are not verified or used.

Imaging unbalance and overexposure: Because of a structural problem of a microscope imaging camera, severe situations such as contrast unbalance and overexposure occur in a captured image, and consequently original image information is lost.

FIG. 1 schematically shows a method 100 for screening microscopic images. In the method 100, a doctor or another medical expert performs repeated precise annotation 102 on an obtained data set 101, and finally deletes 103 an abnormal picture and evaluates picture quality, to eliminate noise information. In many cases, before the data set 101 is used, a large quantity of time needs to be consumed to screen medical images. In a case that a first time of screening is generally not high in quality, the data set further needs to be returned to medical annotation personnel to perform annotation again. Even if no evident error has temporarily been found in data, it is still probable that an abnormal result will be found during later model training. This not only affects accuracy and reliability of a model greatly, but also may require more time costs to check and verify other data before validity, accuracy, and integrity of the data can be confirmed.

Figure 2:
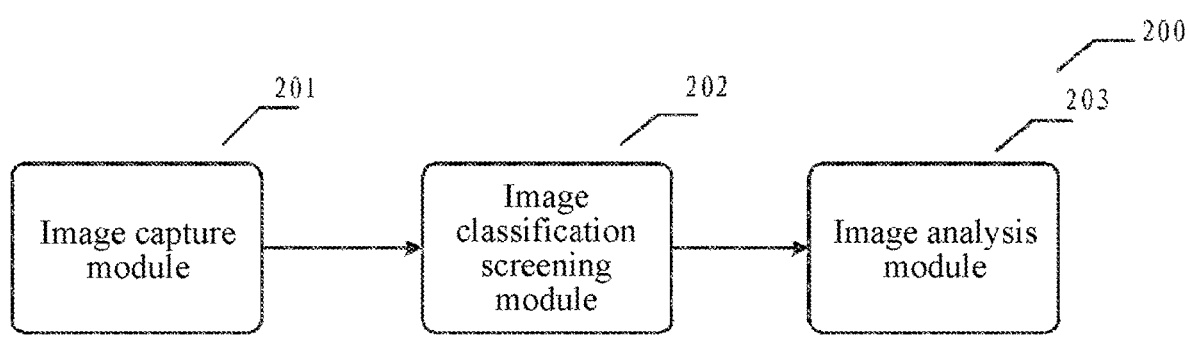
FIG. 2 shows an intelligent microscope system to which an image classification screening module according to an embodiment of this application is applicable.

FIG. 2 schematically shows an intelligent microscope system 200 to which an image classification screening module of this application according to an embodiment of this application is applicable. The intelligent microscope system 200 may include an image capture module 201, an image classification screening module 202, and an image analysis module 203. First, the image capture module 201 obtains a medical image data set. The image classification screening module 202 may include an image filtering module, which is configured to filter out abnormal medical images and allow normal medical images to be selected. The image classification screening module may perform an anomaly detection on medical images in the medical image data set according to this embodiment of this application, to screen out abnormal medical images.

In various embodiments in the present disclosure, "abnormal" or "normal" medical images may not refer to whether one or more tissue or cell in the medical images has a certain disease or not. For example, the abnormal medical images may include an irrelevant tissue, a lens defocus blurred image, a white balance failure image, and the like. These abnormal medical images cannot be used for detecting and finding a disease and therefore need to be deleted from the medical image data set. The normal medical images may be medical images can be used for detecting and finding a disease, and therefore the normal medical images are obtained. Finally, the normal medical images obtained through screening are sent to the image analysis module 203 to further analyze microscopic pathological images, to detect and find a disease according to these normal medical images.

The intelligent microscope system 200 described above with reference to FIG. 2 is mainly configured to obtain data of microscopic pathological images annotated by the medical annotation personnel, which may be not only used for performing data screening on a microscope TNM (tumor, node, metastasis) staging project, but also used by a medical pathological center to archive, confirm, and collate the microscopic pathological images.

Specifically, for an application scenario of the intelligent microscope TNM staging project, before the original medical image data set is applied to a microscopic pathological image analysis system, first, quality analysis needs to be performed on each image in the medical image data set, to extract feature information of each image and remove irrelevant images from the medical image data set according to the extracted feature information, for example, non-pathological images such as a cat or dog image and a nature image; then, anomaly detection and classification are performed on the microscopic pathological images through an image classification screening device, to obtain major categories such as irrelevant tissue, a lens defocus blurred image, cell overlapping or folding, a white balance failure image, a normal medical image, and an irrelevant image, and screen out abnormal images, that is, medical images that cannot be used for detecting and finding a disease, for example, the irrelevant tissue, the lens defocus blurred image, and the white balance failure image; and finally, valid and credible normal medical images obtained through screening are fed into the microscopic pathological image analysis system for analysis, to detect and find a disease according to these normal medical images.

Another application scenario is that the pathological center collates and archives the microscopic images. The image classification screening device according to this application is used to help or replace a doctor to classify various types of pathological microscopic images, to obtain major categories such as irrelevant tissue, a lens defocus blurred image, cell overlapping or folding, a white balance failure image, a normal medical image, and an irrelevant image, and archiving and collating the major categories of medical images obtained through classification may not only help a doctor reduce workload and improve efficiency, but also help detect accuracy of an annotation result.

Figure 3:
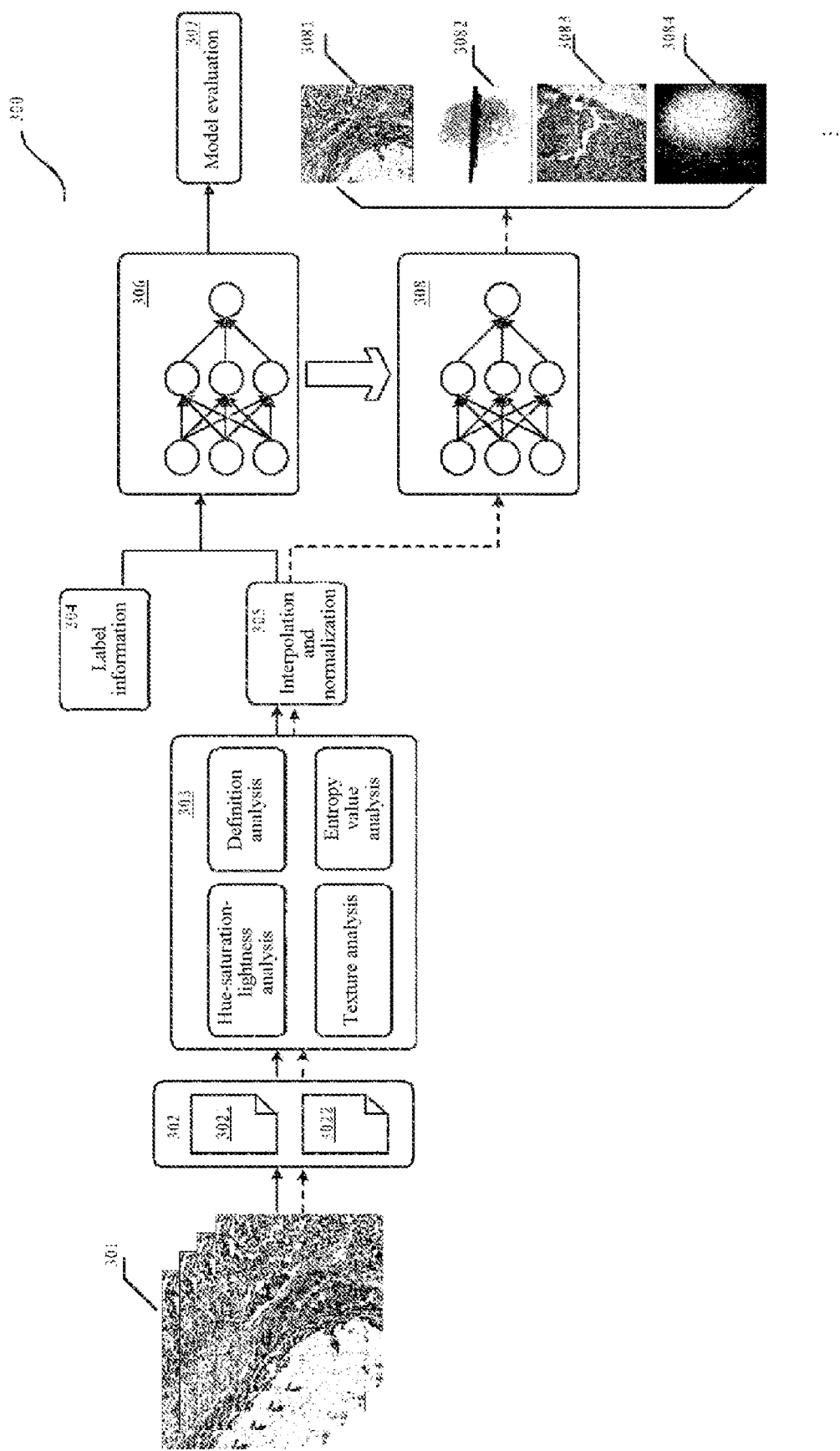
FIG. 3 is a schematic diagram of a model training method according to an embodiment of this application.

FIG. 3 is a schematic diagram of a method 300 for training and testing a model for performing anomaly detection and classification on a medical image according to an embodiment of this application. In FIG. 3, a solid line represents training data, and a dashed line represents testing data. In the training and testing method 300, by establishing a data processing procedure based on digital image processing and deep learning classification algorithms, images such as an irrelevant tissue image, a camera defocus image, a cell overlapping or folding image, and a white balance failure image mixed into a medical image data set are differentiated and deleted, and the data is archived and stored. The medical image data set is the foregoing medical image data set, including at least one medical image. In some embodiments, alternatively, images of different diseases are classified, and image data is archived for the different diseases, which mainly includes the following steps:

(1) A decoding and check module 302 decodes and checks a data set.
(2) A quality analysis module 303 performs one or more of hue analysis, saturation analysis, lightness analysis, definition analysis, texture analysis, and information entropy value analysis on a digital image.
(3) An interpolation and normalization module 305 performs interpolation and normalization on each medical image of the medical image data set.
(4) A deep learning network model 306 is established, the established deep learning network model is trained by using data annotated with annotation information 304 and information extracted by the quality analysis module 303, and the model is stored.
(5) The trained model 306 is loaded into a deep learning network model 308, and testing data that needs to be detected may be screened and classified.

Figure 4A:
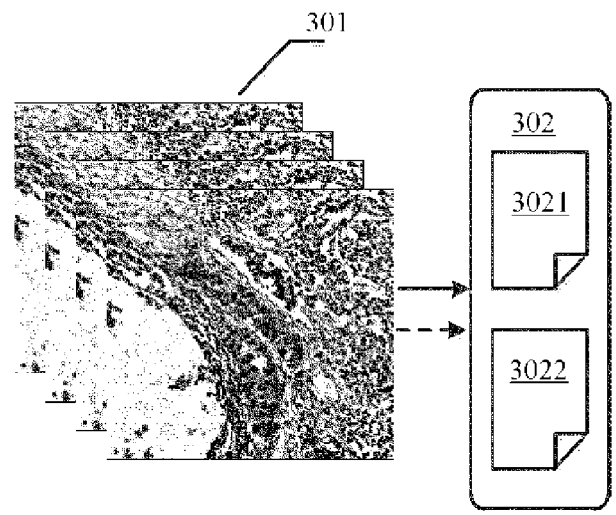
FIG. 4A is a schematic diagram of an original data set and a decoding and file check module.

FIG. 4A is a schematic diagram of an original data set 301 and a decoding and file check module 302. The decoding and file check module 302 includes a file decoding module 3021 and a file check module 3022. Regardless of whether data is training data or testing data, validity check needs to be performed on the data itself, because damage caused to an image itself because of a storage problem or the like is mixed into a data set. Therefore, after the data set of the medical image is obtained, the file decoding module 3021 decodes the image into a digital image matrix for subsequent image processing. The file check module 3022 performs file check on the image, to confirm that a file is capable of being parsed and is not damaged. Such two pieces of check as file check and decoding ensure validity of input data in subsequent processing, and prevent irrelevant data from being mixed into the entire system, which is quite important for the entire solution for anomaly detection and classification according to this application.

Figure 4B:
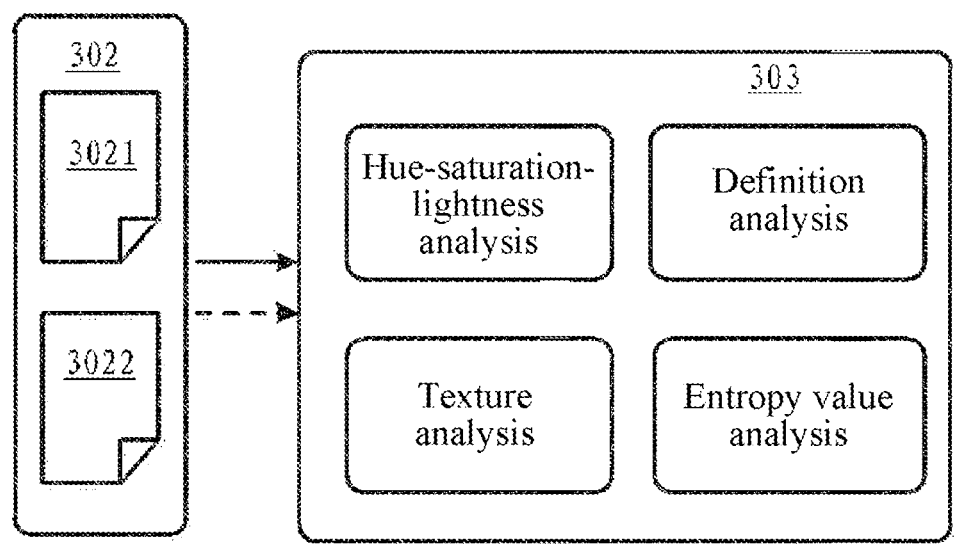
FIG. 4B is a schematic diagram of a quality analysis module.

FIG. 4B is a schematic diagram of a quality analysis module 303. Quality analysis mainly includes hue analysis, saturation analysis, lightness analysis, definition analysis, texture analysis, and entropy value analysis of a digital image matrix. As shown in FIG. 4B, after the digital image matrix subject to decoding 3021 and check 2022 is obtained, various attributes of an image need to be analyzed. Advantages lie in that in an aspect, data helps model classification training, and in another aspect, a majority of irrelevant images may be directly screened out and collated, thereby making subsequent model determination more precise.

Specifically, the hue-saturation-lightness analysis refers to converting an obtained image matrix from an RGB domain to an HSV space, for example, including a hue value, a saturation value, and a lightness value, and conversion formulas are as follows:

$$h = \begin{cases} 0°, & max = min \\ 60° \times \frac{g-b}{max-min} + 0°, & max = r \text{ and } g \geq b \\ 60° \times \frac{g-b}{max-min} + 360°, & max = r \text{ and } g < b \\ 60° \times \frac{b-r}{max-min} + 120°, & max = g \\ 60° \times \frac{r-g}{max-min} + 240°, & max = b \end{cases} \quad (1)$$

$$s \begin{cases} 0, & max = 0 \\ \frac{max-min}{max} = 1 - \frac{min}{max}, & \text{otherwise} \end{cases} \quad (2)$$

$$v = max \quad (3)$$

where (r, g, b) is red, green, and blue coordinates of a point of an image, max is a maximum value of r, g, and b, and min is a minimum value of r, g, and b. In one implementation, values of the red, green, and blue coordinates are real numbers between 0 and 1, inclusive. In another implementation, values of the red, green, and blue coordinates are integers between 0 and 255, inclusive. An average value and a variance of a hue value h matrix, a saturation value s matrix, and a lightness value v matrix are respectively calculated as hue-saturation-lightness feature information expression. As understood by a person skilled in the art, an HSL space may be alternatively used to replace the HSV space, where H represents hue, S represents saturation, and L represents lightness.

Definition may refer to a degree of distinctness in an image. In the definition analysis, assuming that the value of the digital image matrix is a, a convolution value b of a and a 5×5 Gaussian convolution kernel is calculated. Then, a minimum mean square error MSE of a and b is calculated, and a peak signal-to-noise ratio PSNR of the MSE is calculated, where n is a color scale of a medical image, and may be a preset positive integer, for example, the preset value may be a positive integer 8, and the PSNR is selected as a definition index of the image. A calculation formula (4) is as follows:

$$PSNR = 10 \times \log_{10}\left(\frac{(2^n - 1)^2}{MSE}\right). \quad (4)$$

In some other embodiments, the definition analysis may be performed by using a method such as Brenner, Tenengrad, Laplacian, SMD, or SMD2.

In the texture analysis, an edge of a grayscale image is extracted and calculated by using a detection operator such as Sobel or a convolution kernel. As understood by a person skilled in the art, the processing may be alternatively performed by using an operator such as Isotropic Sobel, Roberts, Prewitt, or Laplacian.

In the entropy value analysis, an entropy value is calculated according to a length of the medical image, a width of the medical image, and a quantity of times and a probability that a grayscale value of a center pixel in a sliding window and an average of grayscale values other than that of the center pixel in the sliding window occur in the medical image.

Specifically, assuming that W and H are a length and a width of an image, (i, j) is a two-tuple, i represents a grayscale value of a center pixel in a sliding window, and j is an average of grayscale values other than that of the center pixel in the sliding window; and f(i, j) represents a quantity of times that this two-tuple (i, j) occurs in the entire image, $P_{i,j}$ is a probability that the two-tuple (i, j) occurs in the medical image, and a calculation formula is as follows:

$$\begin{cases} En = -\Sigma_{i=0}^{255} P_{i,j} \log_e P_{i,j} \\ P_{i,j} = f(i, j)/W \cdot H \end{cases} \quad (5)$$

Figure 4C:
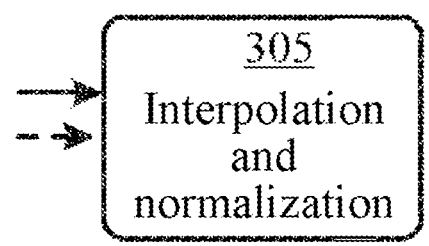
FIG. 4C is a schematic diagram of an interpolation and normalization module.

FIG. 4C is a schematic diagram of an interpolation and normalization module 305. After pre-processing of analyzing image quality is completed, interpolation and normalization need to be performed on an original image, to enable a model to achieve a better training effect. Objectives thereof lie in that, in an aspect, sizes of images in different sizes can be uniformed, to make it convenient to train a network; and in another aspect, all images are uniformed in dimension, to make it convenient to measure and calculate the images. That is to say, the interpolation and normalization module plays a main role in making images dimensionless. Specifically, first, interpolation is performed on each of three channels R, G, and B of an image. Bilinear interpolation is used in this application, to make it convenient to uniform images to the same size. A size of 299×299 (RGB) is used in the system in this application. Then, the image matrix is linearly scaled to fall within a range of [−1, 1]. As understood by a person skilled in the art, interpolation and calculation may be alternatively performed by using a method such as neighbor interpolation or spline interpolation, and the alternative solution may perform data normalization in a manner such as normal normalization.

Figure 4D:
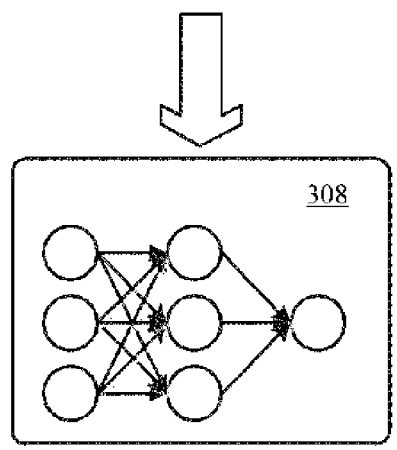
FIG. 4D is a schematic diagram of a to-be-trained deep learning network.

FIG. 4D is a schematic diagram of a to-be-trained deep learning network 308. The foregoing interpolated and normalized data is sent to a to-be-trained deep learning network model, and an image anomaly detection and classification network is trained with reference to annotation information (for example, irrelevant tissue, lens defocus blurred, white balance failure, low-information image, or cell folding or overlapping) provided by a doctor or medical annotation personnel, to obtain a trained deep learning network model. In an embodiment, the deep learning network optimizes the model by using an Inception V3 structure in deep learning and a stochastic gradient descent (SGD) algorithm. Finally, the model is evaluated, and model results that satisfy indexes are selected and stored. A specific process is as follows:

a. Establish an Inception V3 structure of a deep learning network in deep learning.
   b. Set an optimization function for training (that is, an SGD function), and set a learning rate and an iteration count.
   c. Start training a deep learning network model, and detect the learning rate and the iteration count.
   d. Select a model corresponding to a minimum loss value of a verification set loss function, and store the model to be used during testing.

Figure 4E:
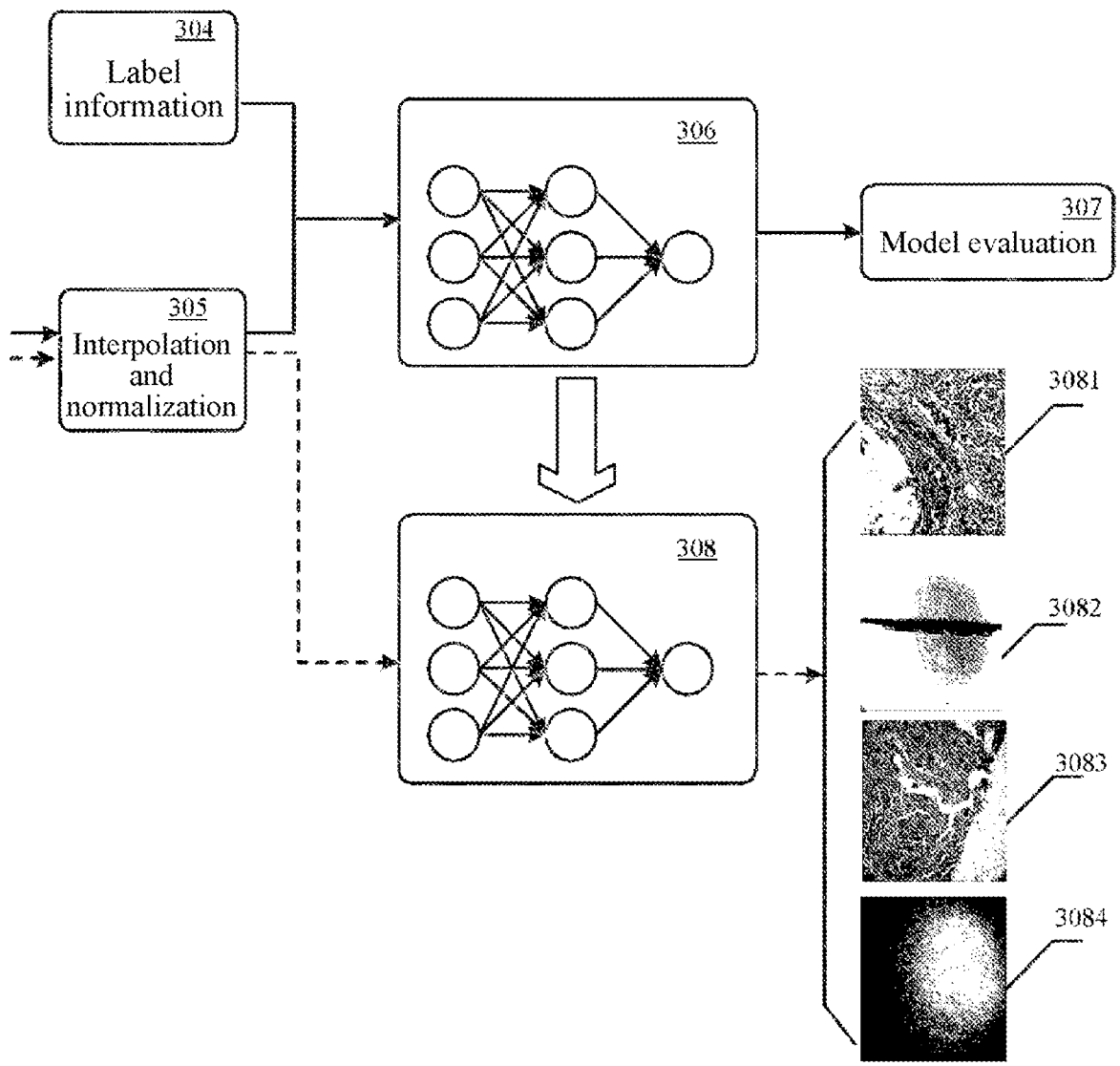
FIG. 4E is a schematic diagram of loading a trained deep learning network model.

FIG. 4E is a schematic diagram of loading a trained deep learning network model. After it is confirmed that the model is trained, the model is loaded, and meanwhile inference is performed on image data on which anomaly classification detection needs to be performed. Corresponding images are filtered and determined by using determination accuracy of the trained model meeting requirements of the loss function, thereby implementing anomaly detection and classification on microscopic pathological images. Specifically, (1) a selected model is loaded; (2) a processed image data set is inputted; (3) a result is outputted and a corresponding result label is generated with reference to the result; and (4) data is stored and archived according to the label.

For model training and determination in FIG. 4D and FIG. 4E, in an alternative embodiment, classification may be performed by using a plurality of types of model structures based on a convolutional neural network. The essence of all of the model structures is feature extraction, feature fusion, and feature determination of the neural network belonging to the same method on an image. As understood by a person skilled in the art, alternatively, feature extraction may be performed by using a conventional image processing algorithm such as SIFT or HOG, classification is performed by using a classifier such as SVM, MLP, or AdaBoost, and the classification and this application essentially jointly belong to a machine learning classification algorithm.

Figure 5A:
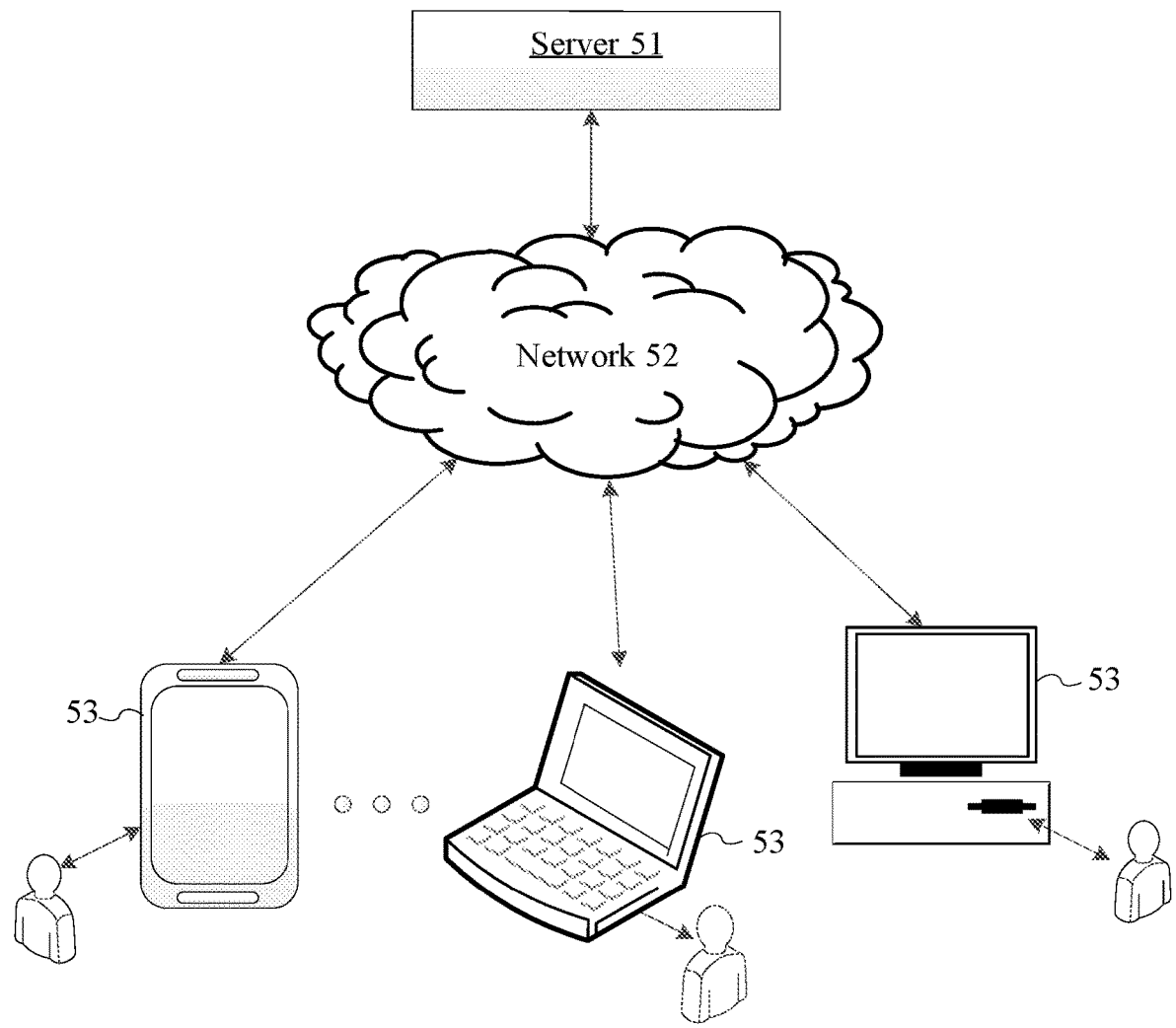
FIG. 5A is an architectural diagram of a system to which a medical image classification method according to an embodiment of this application is applicable.

FIG. 5A is an architectural diagram of a system to which a medical image classification method according to an embodiment of this application is applicable. A server 51 is connected to a user terminal 53 by a network 52.

In some examples of this application, the server 51 is a back-end server for classifying a medical image. The server 51 and the user terminal 53 jointly provide services to a user. For example, after classifying the medical image, the server 51 sends a classification result to the user terminal 53 to be provided to the user for use, and the user may be medical personnel; or in another example, the server 51 may further train a deep learning network for performing anomaly detection and classification on the medical image. The server 51 may be an independent server, or may be a cluster server including a plurality of servers.

The network 52 may include a wired network and a wireless network. As shown in FIG. 5A, on a side of an access network, the user terminal 53 may access the network 52 in a wireless or wired manner. However, on a side of a core network, the server 51 usually accesses the network 52 in a wired manner. Certainly, the server 11 may alternatively be connected to the network 52 in a wireless manner.

The user terminal 53 may refer to a smart device having a data computing processing function, for example, presenting and analyzing information such as the classification result provided by the server, and includes, but is not limited to, a smartphone (in which a communication module is installed), a palmtop computer, a tablet computer, or the like. An operating system is installed on the user terminal 53, including but not limited to, an Android operating system, a Symbian operating system, a Windows mobile operating system, an Apple iPhone OS operating system, and the like.

Figure 5B:
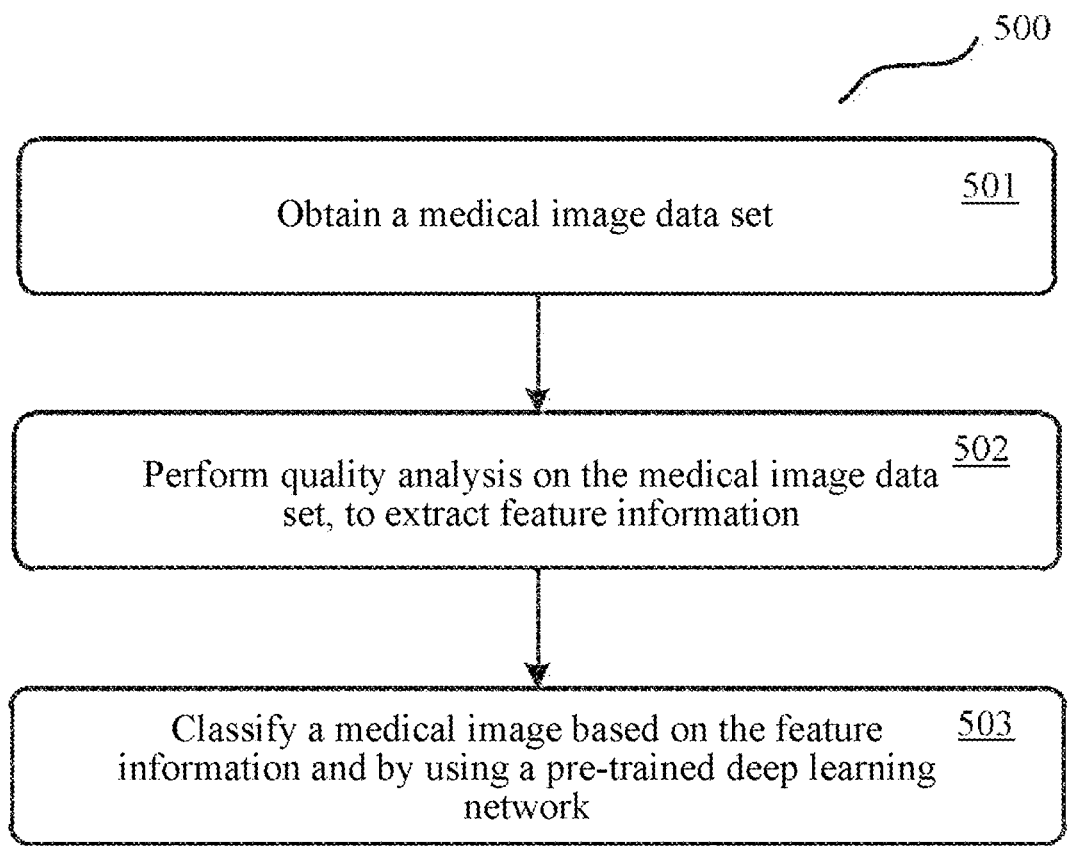
FIG. 5B is a flowchart of an image classification method according to an embodiment of this application.

FIG. 5B is a schematic flowchart of a medical image classification method 500 according to an embodiment of this application. The medical image classification method is performed by a computing device, and the computing device may be the server 51 in FIG. 5A or the user terminal 53 in FIG. 5A. As shown in FIG. 5B, the method includes the following steps.

In step 501, first, obtain a medical image data set. In another implementation, step 501 may include obtaining, by a device comprising a memory storing instructions and a processor in communication with the memory, a medical image data set.

In an embodiment, the medical image data set includes at least one medical image, and after the medical image data set is read, file check and decoding are performed on the obtained medical image data set. Through decoding, the at least one medical image of the medical image data set is converted into a digital image matrix.

In step 502, perform quality analysis on the medical image data set, to extract feature information of a medical image. In another implementation, step 502 may include performing, by the device, quality analysis on the medical image data set, to extract feature information of a medical image in the medical image data set.

In an embodiment, during the performing quality analysis on the medical image data set, to extract feature information of a medical image, at least one of the hue-saturation-lightness analysis, the definition analysis, the texture analysis, and the entropy value analysis is performed on the medical image data set, to obtain the feature information of the medical image, where the feature information of the medical image includes at least one of hue feature information, saturation feature information, lightness feature information, a definition index, a grayscale edge, and an entropy value.

In an embodiment, the quality analysis specifically includes hue-saturation-lightness analysis, definition analysis, texture analysis, and entropy value analysis. Reference may be made to FIG. 3 for the description about the quality analysis. In an embodiment, after the foregoing quality analysis, the medical image data set is interpolated and normalized. In an aspect, sizes of images in different sizes can be uniformed, to make it convenient to train a network; and in another aspect, all images are uniformed in dimension, to make it convenient to measure and calculate the images. That is to say, the interpolation and normalization module plays a main role in making images dimensionless. Specifically, first, interpolation is performed on each of three channels R, G, and B of an image. Bilinear interpolation is used in this application, to make it convenient to uniform images to the same size. A size of 299×299 (RGB) is used in the system in this application. Then, the image matrix is linearly scaled to fall within a range of [−1, 1]. As understood by a person skilled in the art, interpolation and calculation may be alternatively performed by using a method such as neighbor interpolation or spline interpolation, and the alternative solution may perform data normalization in a manner such as normal normalization.

In step 503, classify the medical image based on the extracted feature information and by using a pre-trained deep learning network, to obtain a classification result. In another implementation, step 503 may include classifying, by the device, the medical image data set based on the feature information and by using a pre-trained deep learning network for performing anomaly detection and classification, to obtain a classification result.

In some embodiments, an irrelevant image is removed from the medical image data set according to the extracted feature information, where the irrelevant image includes a non-medical image; and the medical image data set from which the irrelevant image is removed is classified by using the deep learning network for performing anomaly detection and classification on the medical image.

Specifically, an irrelevant image, for example, a non-medical image such as a cat or dog image or a non-pathological nature image is removed from the medical image data set according to the extracted feature information; and the medical image data set from which the irrelevant image is removed is classified by using the deep learning network for performing anomaly detection and classification on the medical image, and an obtained classification result includes such categories as normal tissue, irrelevant tissue, lens defocus, and white balance failure, thereby improving classification precision of the deep learning network.

In some embodiments, after these non-medical images are removed, a majority of irrelevant images of the medical image data set are screened out, but a case that a minority of irrelevant images still remain cannot be excluded; and the medical image data set including the minority of irrelevant images is classified by using the deep learning network for performing anomaly detection and classification on the medical image, and in addition to such categories as normal tissue, irrelevant tissue, lens defocus, and white balance failure, an obtained classification result may further include such a category as irrelevant image.

In some embodiments, it is determined, in a case that the medical image data set includes a medical image whose feature information includes at least one that is of the hue feature information, the saturation feature information, the lightness feature information, the definition index, the grayscale edge, and the entropy value and that is less than a corresponding threshold, that the medical image is the irrelevant image, and the irrelevant image is removed from the medical image data set.

Specifically, provided that the medical image data set includes a medical image whose feature information includes one that is of the hue feature information, the saturation feature information, the lightness feature information, the definition index, the grayscale edge, and the entropy value and that is less than a corresponding threshold, it is determined that the medical image is the irrelevant image.

For example, in a case that saturation feature information of a medical image is less than a threshold corresponding to the saturation feature information, it is determined that the medical image is the irrelevant image, and the irrelevant image is removed from the medical image data set; and in another example, in a case that a definition index of a medical image is less than a threshold corresponding to the definition index and an entropy value of the medical image is less than a threshold corresponding to the entropy value, it is determined that the medical image is the irrelevant image, and the irrelevant image is removed from the medical image data set.

In some embodiments, the classification result includes one or more of categories of normal tissue, irrelevant tissue, lens defocus, white balance failure, and an irrelevant image.

In some embodiments, after a classification result is obtained, the medical image may be classified, archived, and collated according to the obtained classification result.

In some embodiments, after a classification result is obtained, a disease may be detected and found by using a normal medical image in the classification result.

This application provides a complete method for microscopic pathological image processing and feature extraction, to enable an invalid or unqualified pathological image to be filtered out. Therefore, the method purifies microscopic pathological images, to make image-based disease diagnosis more accurate. In another aspect, various morphology attributes of an image are described, making it convenient to archive and collate microscopic pathological images according to quality.

Figure 6:
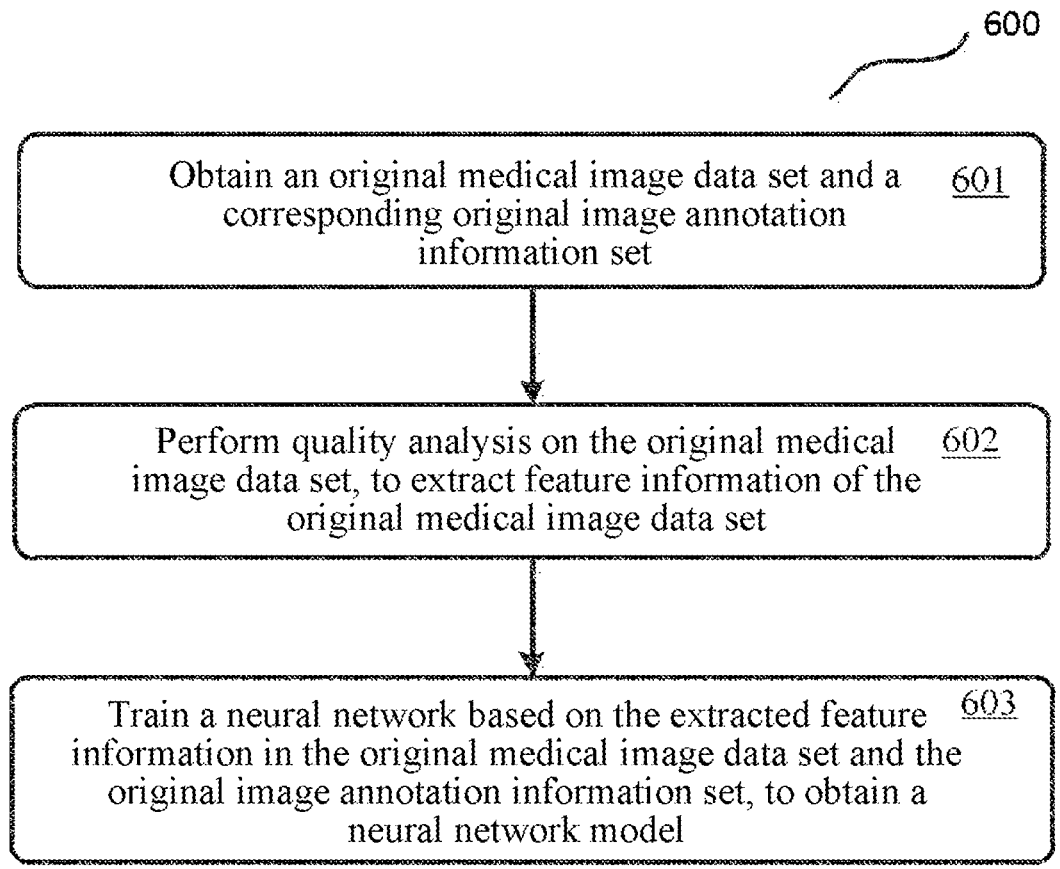
FIG. 6 is a flowchart of a method for training a deep learning network model according to an embodiment of this application.

FIG. 6 is a schematic flowchart of a method 600 for training a deep learning network model according to an embodiment of this application. The training method for a model for performing anomaly detection and classification on a medical image is performed by a computing device, and the computing device may be the server 51 in FIG. 5A or the user terminal 53 in FIG. 5A. As shown in FIG. 6, the method includes the following steps:

In step 601, obtain an original medical image data set and a corresponding original image annotation information set.

In an embodiment, annotation information in the original image annotation information set may be provided by a doctor or medical annotation personnel, and includes a label for a case that the medical image is normal tissue, irrelevant tissue, lens defocus, or white balance failure, which is, for example, irrelevant tissue, lens defocus blurred, white balance failure, low-information image, or cell folding or overlapping. In an embodiment, after the medical image data set is obtained, file check and decoding are performed on the obtained medical image data set. Through decoding, the medical image is converted into a digital image matrix.

In step 602, perform quality analysis on the original medical image data set, to extract feature information of an original medical image.

In an embodiment, the quality analysis may specifically include hue-saturation-lightness analysis, definition analysis, texture analysis, entropy value analysis, and the like. Reference is made to FIG. 3 for details of the description about the quality analysis. In an embodiment, after the foregoing quality analysis, the medical image data set is interpolated and normalized. In an aspect, sizes of images in different sizes can be uniformed, to make it convenient to train a network; and in another aspect, all images are uniformed in dimension, to make it convenient to measure and calculate the images. That is to say, the interpolation and normalization module plays a main role in making images dimensionless. Specifically, first, interpolation is performed on each of three channels R, G, and B of an image. Bilinear interpolation is used in this application, to make it convenient to uniform images to the same size. A size of 299×299 (RGB) is used in the system in this application. Then, the image matrix is linearly scaled to fall within a range of [−1, 1]. As understood by a person skilled in the art, interpolation and calculation may be alternatively performed by using a method such as neighbor interpolation or spline interpolation, and the alternative solution may perform data normalization in a manner such as normal normalization.

In step 603, train, based on the extracted feature information in the original medical image data set and the original image annotation information set, a deep learning network, to obtain a deep learning network model.

Figure 7:
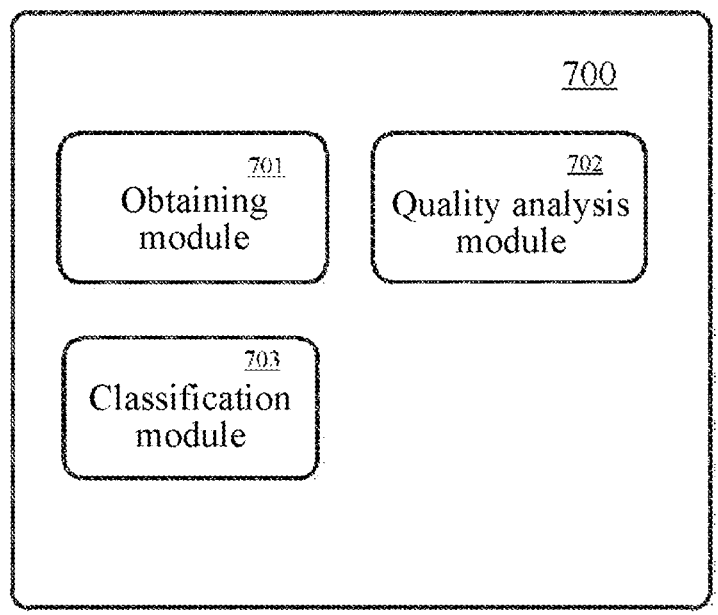
FIG. 7 is a schematic diagram of a medical image classification server according to an embodiment of this application.

FIG. 7 is a schematic diagram of a medical image classification apparatus 700 according to an embodiment of this application. The apparatus 700 includes an obtaining module 701, a quality analysis module 702, and a classification module 703. The obtaining module 701 is configured to obtain a medical image data set. The quality analysis module 702 is configured to perform quality analysis on the medical image data set, to extract feature information of the medical image. The classification module 703 is configured to classify the medical image based on the extracted feature information and by using a pre-trained deep learning network, to obtain a classification result.

Figure 8:
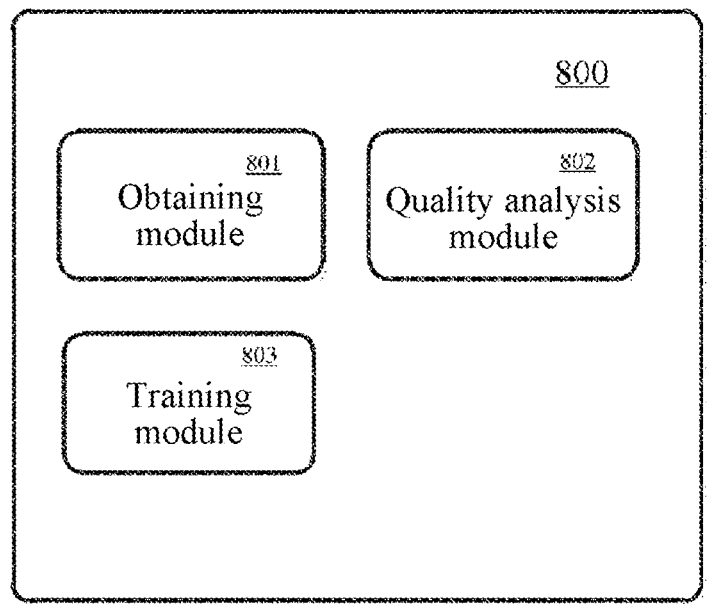
FIG. 8 is a schematic diagram of a server for training a deep learning network model according to an embodiment of this application.

FIG. 8 is a schematic diagram of an apparatus 800 for training a model for performing anomaly detection and classification on a medical image according to an embodiment of this application. The apparatus 800 includes an obtaining module 801, a quality analysis module 802, and a training module 803. The obtaining module 801 is configured to obtain an original medical image data set and a corresponding original image annotation information set. The quality analysis module 802 is configured to perform quality analysis on the original medical image data set, to extract feature information of an original medical image. The training module 803 is configured to train, based on the extracted feature information in the original medical image data set and the original image annotation information set, a deep learning network for performing anomaly detection and classification on the medical image, to obtain a trained deep learning network model for performing anomaly detection and classification on the medical image.

Figure 9:
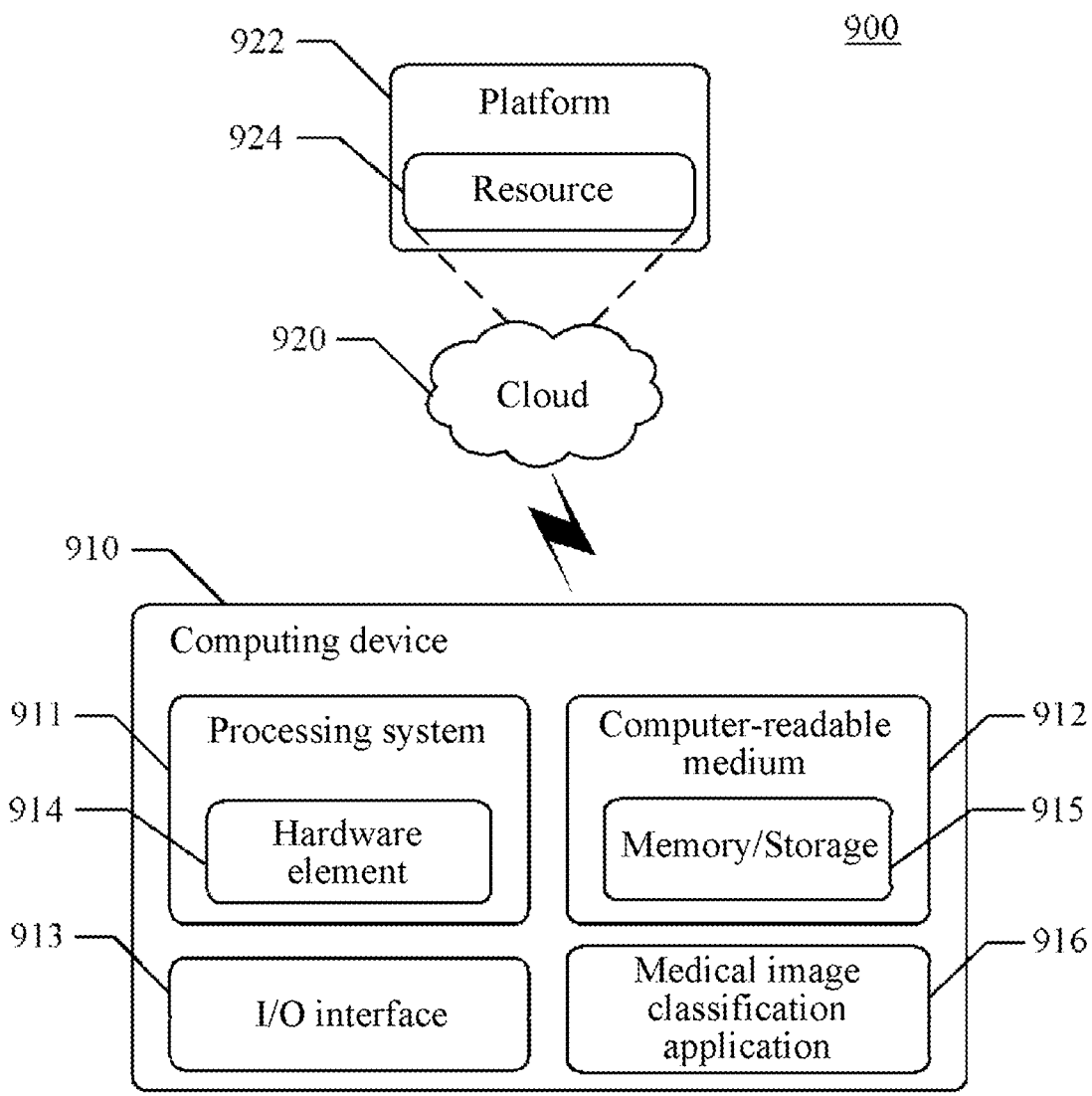
FIG. 9 shows an exemplary system, including an exemplary computing device representing one or more systems and/or devices that may implement various technologies described in this specification.

FIG. 9 shows an exemplary system 900, including an exemplary computing device 910 representing one or more systems and/or devices that may implement various technologies described in this specification. The computing device 910 may be, for example, a server of a service provider, a device associated with a client (for example, a client device), a system-on-chip, and/or any other appropriate computing device or computing system. The medical image classification server 700 in FIG. 7 or the server 800 for training a deep learning network model in FIG. 8 may be in the form of the computing device 910. Alternatively, the medical image classification server 700 or the server 800 for training a deep learning network model in FIG. 8 may be implemented as a computer program in the form of a medical image classification application 916.

The shown exemplary computing device 910 includes a processing system 911, one or more computer-readable mediums 912, and one or more I/O interfaces 913 communicatively coupled to each other. Although not shown, the computing device 910 may further include a system bus or another data and command transfer system, to couple various components to each other. The system bus may include any one of or a combination of different bus structures, and the bus structures include, for example, a memory bus or memory controller, a peripheral bus, a universal serial bus, and/or a processor or local bus using any one of various bus architectures. Various other examples such as a control and data lines are further contemplated.

The processing system 911 is representative of functionality to perform one or more operations by using hardware. Therefore, the processing system 911 is illustrated as including hardware elements 914 that may be configured as processors or functional blocks. This may include being implemented in hardware as an application-specific integrated circuit or another logic device formed by using one or more semiconductors. The hardware elements 914 are not limited by the materials from which they are formed or the processing mechanisms employed therein. For example, the processors may be formed by semiconductor(s) and/or transistors (for example, electronic integrated circuits (ICs)). In such a context, processor-executable instructions may be electronically-executable instructions.

The computer-readable medium 912 is illustrated as including a memory/storage 915. The memory/storage 915 represents memory/storage capacity associated with one or more computer-readable media. The memory/storage 915 may include volatile media (such as a random access memory (RAM)) and/or nonvolatile media (such as a read only memory (ROM), flash memory, optical discs, magnetic disks, and the like). The memory/storage 915 may include fixed media (for example, RAM, ROM, a fixed hard drive, and so on) and removable media (for example, flash memory, a removable hard drive, an optical disc, and the like). The computer-readable medium 912 may be configured in a variety of other ways as further described below.

One or more I/O interfaces 913 are representative of functionality to allow a user to enter commands and information to the computing device 910, and also allow information to be presented to the user and/or other components or devices using various input/output devices. Examples of input devices include a keyboard, a cursor control device (for example, a mouse), a microphone (for example, used for voice input), a scanner, touch functionality (for example, capacitive or other sensors that are configured to detect physical touch), a camera (for example, which may employ visible or non-visible wavelengths such as infrared frequencies to recognize movements that do not involve touch as gestures), and the like. Examples of output devices include a display device (for example, a monitor or projector), a speaker, a printer, a network card, a tactile-response device, and the like. Thus, the computing device 910 may be configured in a variety of ways as further described below to support user interaction.

The computing device 910 further includes the medical image classification application 916. The medical image classification application 916 may be, for example, a software example of the medical image classification server 700 in FIG. 7 or the model training server 800 in FIG. 8, and implements the technology described in this specification in combination with other elements in the computing device 910.

Various technologies may be described herein in the general context of software, hardware elements, or program modules. Generally, the modules include a routine, a program, an object, an element, a component, a data structure, and the like for executing a particular task or implementing a particular abstract data type. The terms "module", "functionality", and "component" as used herein generally represent software, firmware, hardware, or a combination thereof. The features of the technologies described herein are platform-independent, meaning that the technologies may be implemented on a variety of computing platforms having a variety of processors.

An implementation of the described modules and technologies may be stored on or transmitted across some form of computer-readable media. The computer-readable media may include a variety of media that may be accessed by the computing device 910. By way of example, and not limitation, computer-readable media may include "computer-readable storage media" and "computer-readable signal media".

"Computer-readable storage media" refers to media and/or devices that enable persistent storage of information and/or tangible storage in contrast to mere signal transmission, carrier waves, or signals. Thus, computer-readable storage media refer to non-signal bearing media. The computer-readable storage media include hardware such as volatile and non-volatile, removable and non-removable media and/or storage devices implemented in a method or technology suitable for storage of information (such as computer-readable instructions, data structures, program modules, logic elements/circuits, or other data). Examples of computer-readable storage media may include, but are not limited to, RAM, ROM, EEPROM, flash memory or other memory technology, CD-ROM, digital versatile disk (DVD) or other optical storage, hard disks, magnetic cassettes, magnetic tape, magnetic disk storage or other magnetic storage devices, or other storage device, tangible media, or article of manufacture that is suitable to store the expected information and which may be accessed by a computer.

The "computer-readable signal medium" refers to a signal-bearing medium that is configured to transmit instructions to the hardware of the computing device 910, such as via a network. Signal media typically may embody computer-readable instructions, data structures, program modules, or other data in a modulated data signal, such as a carrier wave, a data signal, or another transport mechanism. Signal media further include any information delivery media. The term "modulated data signal" refers to a signal that has one or more of its characteristics that are set or changed in such a manner as to encode information in the signal. By way of example, and not limitation, communication media include wired media such as a wired network or direct-wired connection, and wireless media such as acoustic, RF, infrared, and other wireless media.

As previously described, the hardware elements 914 and the computer-readable medium 912 are representative of instructions, modules, programmable device logic and/or fixed device logic implemented in a hardware form that may be employed in some embodiments to implement at least some aspects of the technologies described herein. Hardware elements may include components of an integrated circuit or system-on-chip, an application-specific integrated circuit (ASIC), a field-programmable gate array (FPGA), a complex programmable logic device (CPLD), and other implementations in silicon or other hardware devices. In this context, hardware elements may operate as a processing device that performs program tasks defined by instructions, modules, and/or logic embodied by the hardware elements as well as a hardware device utilized to store instructions for execution, for example, the computer-readable storage media described previously.

Combinations of the foregoing may also be employed to implement various technologies and modules described herein. Accordingly, software, hardware or program modules, and other program modules may be implemented as one or more instructions and/or logic embodied on some form of computer-readable storage media and/or by one or more hardware elements 914. The computing device 910 may be configured to implement particular instructions and/or functions corresponding to the software and/or hardware modules. Accordingly, implementation of a module that is executable by the computing device 910 as software may be achieved at least partially in hardware, for example, through use of computer-readable storage media and/or hardware elements 914 of the processing system. The instructions and/or functions may be executable/operable by one or more articles of manufacture (for example, one or more computing devices 910 and/or processing systems 911) to implement technologies, modules, and examples described herein.

In various implementations, the computing device 910 may use various different configurations. For example, the computing device 910 may be implemented as including computer devices such as a personal computer, a desktop computer, a multi-screen computer, a laptop computer, and a netbook. The computing device 910 may be alternatively implemented as a mobile apparatus-type device including a mobile device such as a mobile phone, a portable music player, a portable game device, a tablet computer, or a multi-screen computer. The computing device 910 may be alternatively implemented as a television-type device, including devices that have or are connected to usually larger screens in leisure viewing environments. These devices include televisions, set-top boxes, gaming consoles, and so on.

The technologies described herein may be supported by various configurations of the computing device 910 and are not limited to the specific examples of the technologies described herein. This functionality may also be implemented all or in part through use of a distributed system, such as over a "cloud" 920 via a platform 922 as described below.

The cloud 920 includes and/or is representative of the platform 922 for resources 924. The platform 922 abstracts underlying functionality of hardware (for example, servers) and software resources of the cloud 920. The resources 924 may include applications and/or data that can be utilized while computer processing is executed on servers that are remote from the computing device 910. The resources 924 can also include services provided over the Internet and/or through a subscriber network, such as a cellular or Wi-Fi network.

The platform 922 may abstract resources and functions to connect the computing device 910 with other computing devices. The platform 922 may also serve to abstract scaling of resources to provide a corresponding level of scale to encountered demand for the resources 924 that are implemented via the platform 922. Accordingly, in an interconnected device embodiment, implementation of functionality described herein may be distributed throughout the system 900. For example, the functionality may be implemented in part on the computing device 910 as well as via the platform 922 that abstracts the functionality of the cloud 920.

It is to be understood that, for clarity, the embodiments of this application are described with reference to different function modules. However, evidently, without deviating from this application, the functionality of each function module may be implemented in a single module, implemented in a plurality of modules, or implemented as a part of another function module. For example, the functionality described as being performed by a single module may be performed by a plurality of different modules. Therefore, reference to a particular function module is only considered as reference to a proper module used for providing the described functionality, but does not indicate a strictly logical or physical structure or organization. Therefore, this application may be implemented in a single module, or may be physically and functionally distributed between different modules and circuits.

It is to be understood that, although terms such as first, second, and third may be used for describing various devices, elements, or components in this specification, these devices, elements, or components are not to be limited by these terms. These terms are only used for differentiating between a device, element, or component and another device, element, or component.

Although this application is described with reference to some embodiments, the embodiments do not aim to limit this application to the particular forms described in this specification. On the contrary, the scope of this application is subject only to the appended claims. Additionally, although individual features may be included in different claims, these features may possibly be advantageously combined, and the inclusion in different claims does not imply that a combination of features is not feasible and/or advantageous. The order of features in the claims does not imply any particular order in which the features need to be performed. In addition, in the claims, the term "comprising" does not exclude other elements, and the indefinite article "a" or "an" does not exclude a plurality. Reference signs in the claims are provided only as definite examples, and are not to be construed as limiting the scope of the claims in any manner.

What is claimed is:

1. A method for classifying a medical image, the method comprising:
   obtaining, by a device comprising a memory storing instructions and a processor in communication with the memory, a medical image data set;
   performing, by the device, quality analysis on the medical image data set, to extract feature information of a medical image in the medical image data set, the quality analysis comprising at least one of the following: hue-saturation-lightness analysis, definition analysis, texture analysis, or entropy value analysis, by:
      performing, by the device, at least one of the following: the hue-saturation-lightness analysis, the definition analysis, the texture analysis, or the entropy value analysis on the medical image data set, to extract the feature information of the medical image, wherein the feature information comprises at least one of the following: hue feature information, saturation feature information, lightness feature information, a definition index, a grayscale edge, or an entropy value; and
   classifying, by the device, the medical image data set based on the feature information and by using a pre-trained deep learning network for performing anomaly detection and classification, to obtain a classification result,
   wherein:
      performing the hue-saturation-lightness analysis comprises converting values of a red coordinate, a green coordinate, and a blue coordinate of the medical image from an RGB space to an HSV space, to obtain hue feature information, saturation feature information, and lightness feature information;
      performing the definition analysis comprises:
         calculating a value of a digital image matrix of the medical image,
         performing convolution on the value of the digital image matrix and a 5×5 Gaussian convolution kernel to obtain a convolution value, and
         calculating a definition index of the medical image based on a minimum mean square error of the value of the digital image matrix and the convolution value;
      performing the texture analysis comprises extracting a grayscale edge of the medical image by using a Sobel verification operator; and
      performing the entropy value analysis comprises calculating an entropy value according to a length of the medical image, a width of the medical image, and a quantity of times and a probability that a grayscale value of a center pixel in a sliding window and an average of grayscale values other than that of the center pixel in the sliding window occur in the medical image.

2. The method according to claim 1, wherein the classifying the medical image data set based on the feature information and by using the pre-trained deep learning network for performing anomaly detection and classification comprises:
   removing, by the device, an irrelevant image from the medical image data set according to the feature information, wherein the irrelevant image comprises a non-medical image; and
   classifying, by the device using the pre-trained deep learning network for performing anomaly detection and classification, the medical image data set from which the irrelevant image is removed.

3. The method according to claim 1, further comprising:
   before performing the quality analysis:
      performing, by the device, file check on the medical image data set to determine whether the medical image in the medical image data set is capable of being parsed; and
      in response to determining that whether the medical image in the medical image data set is capable of being parsed, decoding, by the device, the medical image data set to convert the medical image into a digital image matrix.

4. The method according to claim 1, further comprising:
   before classifying the medical image data set, performing, by the device, interpolation and normalization on the medical image in the medical image data set, wherein the interpolation comprises bilinear interpolation.

5. The method according to claim 1, further comprising:
   training, by the device, the pre-trained deep learning network by selecting an Inception V3 model.

6. An apparatus for classifying a medical image, the apparatus comprising:
   a memory storing instructions; and
   a processor in communication with the memory, wherein, when the processor executes the instructions, the processor is configured to cause the apparatus to:
      obtain a medical image data set,
      perform quality analysis on the medical image data set, to extract feature information of a medical image in the medical image data set, the quality analysis comprises at least one of the following: hue-saturation-lightness analysis, definition analysis, texture analysis, or entropy value analysis, by:
         performing at least one of the following: the hue-saturation-lightness analysis, the definition analysis, the texture analysis, or the entropy value analysis on the medical image data set, to extract the feature information of the medical image, wherein the feature information comprises at least one of the following: hue feature information, saturation feature information, lightness feature information, a definition index, a grayscale edge, or an entropy value, and classify the medical image data set based on the feature information and by using a pre-trained deep learning network for performing anomaly detection and classification, to obtain a classification result, wherein:
when the processor is configured to cause the apparatus to perform the hue-saturation-lightness analysis, the processor is configured to cause the apparatus to convert values of a red coordinate, a green coordinate, and a blue coordinate of the medical image from an RGB space to an HSV space, to obtain hue feature information, saturation feature information, and lightness feature information;

when the processor is configured to cause the apparatus to perform the definition analysis, the processor is configured to cause the apparatus to:
calculate a value of a digital image matrix of the medical image,
perform convolution on the value of the digital image matrix and a 5×5 Gaussian convolution kernel to obtain a convolution value, and
calculate a definition index of the medical image based on a minimum mean square error of the value of the digital image matrix and the convolution value;

when the processor is configured to cause the apparatus to perform the texture analysis, the processor is configured to cause the apparatus to extract a grayscale edge of the medical image by using a Sobel verification operator; and when the processor is configured to cause the apparatus to perform the entropy value analysis, the processor is configured to cause the apparatus to calculate an entropy value according to a length of the medical image, a width of the medical image, and a quantity of times and a probability that a grayscale value of a center pixel in a sliding window and an average of grayscale values other than that of the center pixel in the sliding window occur in the medical image.

7. The apparatus according to claim 6, wherein, when the processor is configured to cause the apparatus to classify the medical image data set based on the feature information and by using the pre-trained deep learning network for performing anomaly detection and classification, the processor is configured to cause the apparatus to:
remove an irrelevant image from the medical image data set according to the feature information, wherein the irrelevant image comprises a non-medical image; and
classify, by using the pre-trained deep learning network for performing anomaly detection and classification, the medical image data set from which the irrelevant image is removed.

8. The apparatus according to claim 6, wherein, before the processor is configured to cause the apparatus to perform the quality analysis, the processor is configured to further cause the apparatus to:
perform file check on the medical image data set to determine whether the medical image in the medical image data set is capable of being parsed; and
in response to determining that whether the medical image in the medical image data set is capable of being parsed, decode the medical image data set to convert the medical image into a digital image matrix.

9. The apparatus according to claim 6, wherein, before the processor is configured to cause the apparatus to classify the medical image data set, the processor is configured to further cause the apparatus to:
perform interpolation and normalization on the medical image in the medical image data set, wherein the interpolation comprises bilinear interpolation.

10. The apparatus according to claim 6, wherein, when the processor executes the instructions, the processor is configured to further cause the apparatus to:
train the pre-trained deep learning network by selecting an Inception V3 model.

11. A non-transitory computer-readable storage medium, storing computer-readable instructions, wherein, the computer-readable instructions, when executed by a processor, are configured to cause the processor to perform:
obtaining a medical image data set;
performing quality analysis on the medical image data set, to extract feature information of a medical image in the medical image data set, the quality analysis comprising at least one of the following: hue-saturation-lightness analysis, definition analysis, texture analysis, or entropy value analysis, by:
performing at least one of the following: the hue-saturation-lightness analysis, the definition analysis, the texture analysis, or the entropy value analysis on the medical image data set, to extract the feature information of the medical image, wherein the feature information comprises at least one of the following: hue feature information, saturation feature information, lightness feature information, a definition index, a grayscale edge, or an entropy value; and
classifying the medical image data set based on the feature information and by using a pre-trained deep learning network for performing anomaly detection and classification, to obtain a classification result, wherein:
when the computer-readable instructions are configured to cause the processor to perform performing the hue-saturation-lightness analysis, the computer-readable instructions are configured to cause the processor to perform converting values of a red coordinate, a green coordinate, and a blue coordinate of the medical image from an RGB space to an HSV space, to obtain hue feature information, saturation feature information, and lightness feature information;

when the computer-readable instructions are configured to cause the processor to perform performing the definition analysis, the computer-readable instructions are configured to cause the processor to perform:
calculating a value of a digital image matrix of the medical image,
performing convolution on the value of the digital image matrix and a 5×5 Gaussian convolution kernel to obtain a convolution value, and
calculating a definition index of the medical image based on a minimum mean square error of the value of the digital image matrix and the convolution value;

when the computer-readable instructions are configured to cause the processor to perform performing the texture analysis, the computer-readable instructions are configured to cause the processor to perform extracting a grayscale edge of the medical image by using a Sobel verification operator; and when the computer-readable instructions are configured to cause the processor to perform performing the entropy value analysis, the computer-readable instructions are configured to cause the processor to perform calculating an entropy value according to a length of the medical image, a width of the medical image, and a quantity of times and a probability that a grayscale value of a center pixel in a sliding window and an average of grayscale values other than that of the center pixel in the sliding window occur in the medical image.

12. The non-transitory computer-readable storage medium according to claim 11, wherein, when the computer-readable instructions are configured to cause the processor to perform classifying the medical image data set based on the feature information and by using the pre-trained deep learning network for performing anomaly detection and classification, the computer-readable instructions are configured to cause the processor to perform:
　removing an irrelevant image from the medical image data set according to the feature information, wherein the irrelevant image comprises a non-medical image; and
　classifying, by using the pre-trained deep learning network for performing anomaly detection and classification, the medical image data set from which the irrelevant image is removed.

13. The non-transitory computer-readable storage medium according to claim 11, wherein, before the computer-readable instructions are configured to cause the processor to perform performing the quality analysis, the computer-readable instructions are configured to further cause the processor to perform:
　performing file check on the medical image data set to determine whether the medical image in the medical image data set is capable of being parsed; and
　in response to determining that whether the medical image in the medical image data set is capable of being parsed, decoding the medical image data set to convert the medical image into a digital image matrix.

14. The non-transitory computer-readable storage medium according to claim 11, wherein, before the computer-readable instructions are configured to cause the processor to perform classifying the medical image data set, the computer-readable instructions are configured to further cause the processor to perform:
　performing interpolation and normalization on the medical image in the medical image data set, wherein the interpolation comprises bilinear interpolation.

\* \* \* \* \*